United States Patent [19]

Antebi

[11] Patent Number: 4,592,355
[45] Date of Patent: Jun. 3, 1986

[54] PROCESS FOR TYING LIVE TISSUE AND AN INSTRUMENT FOR PERFORMING THE TYING OPERATION

[76] Inventor: Eliahu Antebi, 22 Ehud Street, Tel Aviv 69936, Israel

[21] Appl. No.: 571,591

[22] Filed: Jan. 17, 1984

[30] Foreign Application Priority Data

Jan. 28, 1983 [IL] Israel .................................. 67773

[51] Int. Cl.$^4$ ............................................. A61B 17/12
[52] U.S. Cl. .................................................... 128/326
[58] Field of Search ...................... 128/326, 335.5, 325, 128/327, 346, 347

[56] References Cited

U.S. PATENT DOCUMENTS 3,985,138  10/1976  Jarvik ................................. 128/326
4,018,229  4/1977  Komiya ............................... 128/326

OTHER PUBLICATIONS

Product Catalogue 9–81 of All States Plastic Mfg. Co., Inc., Entitled "Engineered Fasteners", pp. 4–5 (1980).

Primary Examiner—Jay N. Eskovitz
Attorney, Agent, or Firm—Leydig, Voit & Mayer, Ltd.

[57] ABSTRACT

A process for tying live tissue and an instrument used in performing the tying operation. The tie is of the type comprising a toothed strap having an apertured head at one end, the other end of the strap being threaded through the head and locked therein by a pawl. The instrument comprises an extension having a fork-like construction for holding the head of the looped tie, a rod adapted to be moved relative to the extension and having a buckle-like construction for holding the free end of the strap, and a handle for effecting the movement of the rod relative to the extension whereby the strap is pulled through the head of the tie so as to tighten the loop around the live tissue.

3 Claims, 4 Drawing Figures

PROCESS FOR TYING LIVE TISSUE AND AN INSTRUMENT FOR PERFORMING THE TYING OPERATION

BACKGROUND OF THE INVENTION

The present invention relates generally to a process for tying live tissue and to the instrument used in performing the tying operation. The process and instrument are suitable for a broad range of medical applications, and are especially advantageously employed in the treatment of hemorrhoidal tissues.

The tying of live tissue has become commonplace in performing various medical operations. Oftentimes, the tying is intended to occlude the vascular supply to the tissue, so that the tissue will become necrotic and slough off. This procedure is most commonly used in the treatment of hemorrhoids. The present invention will therefore be described in the context of a hemorrhoidectomy, though it should be understood that the invention is not limited to the ligation of hemorrhoidal tissues.

Presently, hemorrhoids are removed surgically or by rubber band ligation. This latter treatment does not require a general anesthetic and is routinely performed on an an ambulatory basis. In the course of this treatment, extended rubber bands are mounted on an instrument designed specifically for this operation. The rubber bands are then slipped past the bulging hemorrhoidal tissue and released from the instrument. When released, the rubber bands contract and tie off the tissue. In practice, this method suffers from numerous disadvantages. Mounting the rubber bands on the instrument can be difficult and tedious, particularly in an operating room where the personnel are required to wear gloves to ensure strict hygiene. In addition, the rubber bands may break or permanently deform if they are stretched beyond their elastic limits. This latter situation could severely impair the effectiveness of the ligation.

Another disadvantage of the above described method is that large hemorrhoids cannot be ligated due to the physical constraints of the instruments on which the rubber bands are mounted. Typically these instruments cannot extend a rubber band beyond 12 mm in diameter, making the ligation of hemorrhoidal tissue exceeding that size difficult, if not altogether impossible.

Accordingly, it is an object of the present invention to provide a process for the ligation of live tissue without resort to rubber bands or similar elastomeric materials. It is a related object of the invention to provide a process and an instrument for tying live tissue notwithstanding the size of the tissue to be tied.

Other objects and advantages of the invention will become apparent upon reading the attached detailed description and upon reference to the drawings.

DETAILED DESCRIPTION

While the invention has been described in connection with a preferred embodiment, it will be understood that I do not intend to be limited to the particular embodiment shown but intend, on the contrary, to cover the various alternative and equivalent constructions which may be included within the spirit and scope of the appended claims.

Turning now to the drawings, there is shown in the figures a tie denoted generally as 10 and an instrument for tying live tissue denoted generally as 20. While the instrument according to the invention may be advantageously employed in virtually any operation involving the tying of live tissue, the following detailed description describes the instrument as it is used in the treatment of hemorrhoidal tissues, and the process according to the invention is described in the context of a hemorrhoidectomy.

The process comprises the steps of forming a loop in a tie of the type comprising a toothed strap having an apertured head at one end. The loop is formed by threading the other end of the strap through the head, the strap being locked therein by a pawl. The loop is then placed around the hemorrhoidal tissue and tightened by pulling the strap through the head.

The instrument for performing the tying operation comprises an extension having means for holding the head of the looped tie. A rod, adapted to be moved relative to the extension, has means for holding the free end of the strap. A handle is provided to effect the movement of the rod relative to the extension whereby the strap may be pulled through the head so as to tighten the loop around the hemorrhoidal tissue.

Figure 1:
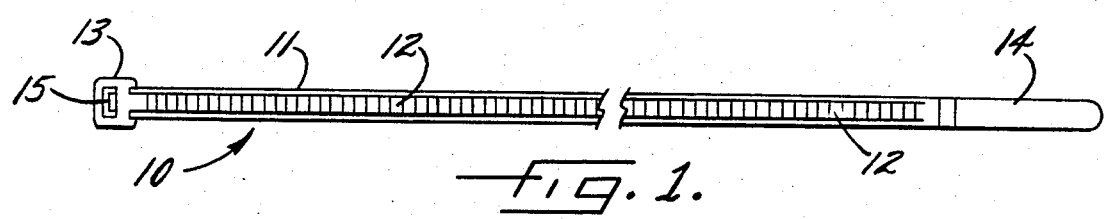
FIG. 1 is a plan view of a tie according to the invention in the open condition.
Figure 2:
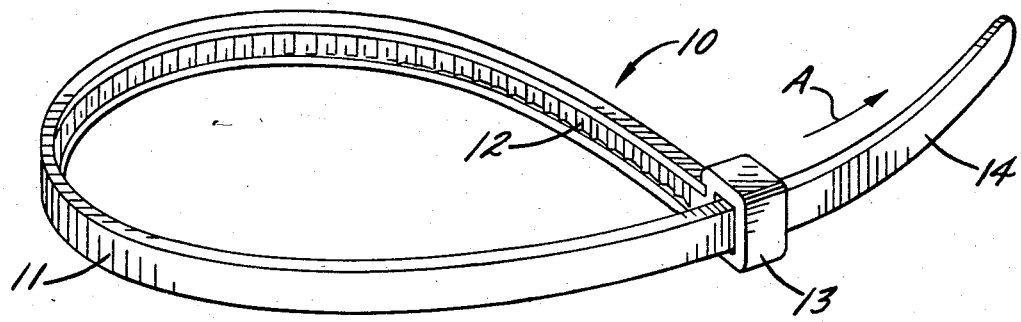
FIG. 2 is a similar plan view of the tie in the threaded condition.

An example of the tie to be used in the present invention is shown in FIG. 1. The tie comprises a strap 11 with teeth 12 having an apertured head 13 at one end. As shown in FIG. 2, a loop may be made by threading the other end 14 of the toothed strap 11 through the head 13, the strap being locked therein by a pawl 15. The loop is prevented from opening by the engagement of the teeth 12 with the pawl 15, and may be made smaller by continuing to thread the strap 11 through the opening in the head 13 in the direction of arrow A. Such ties are routinely used in closing plastic bags and the like, and for securing a bundle of electrical wires or cables into a harness (see for example U.S. Pat. 3,605,199 to Robert Eberhardt), and are available from All States Plastic Manufacturing Company, Inc. under the trademark RAP-TIGHT ® Cable Ties.

RAP-TIGHT ® Cable Ties RT350 and RT360 are considered to be particularly suitable for use in the present invention. RT350 has an overall length of 94.4 mm, a width of 2.1 mm, and a thickness of 1.1 mm. The minimum and maximum loop or bundle diameters are 1.5 mm and 19 mm, respectively, and the minimum loop tensile strength is 8.1 kg. RT360 has an overall length of 149.2 mm, a width of 2.1 mm, and a thickness of 1.1 mm. The minimum and maximum loop or bundle diameters are 19.0 mm and 38.1 mm, respectively, and the minimum loop tensile strength is 8.1 kg.

Figure 3:
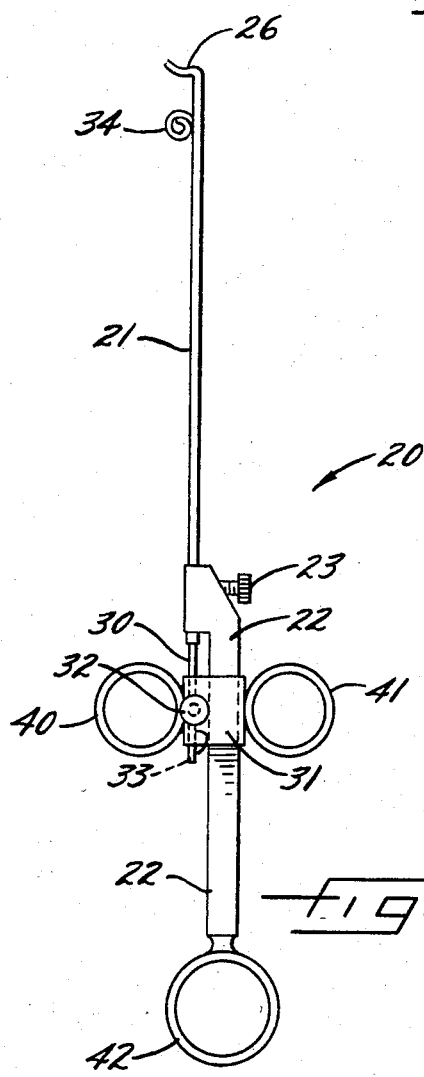
FIG. 3 is a side elevation of the instrument used for tying live tissue according to the invention.
Figure 4:
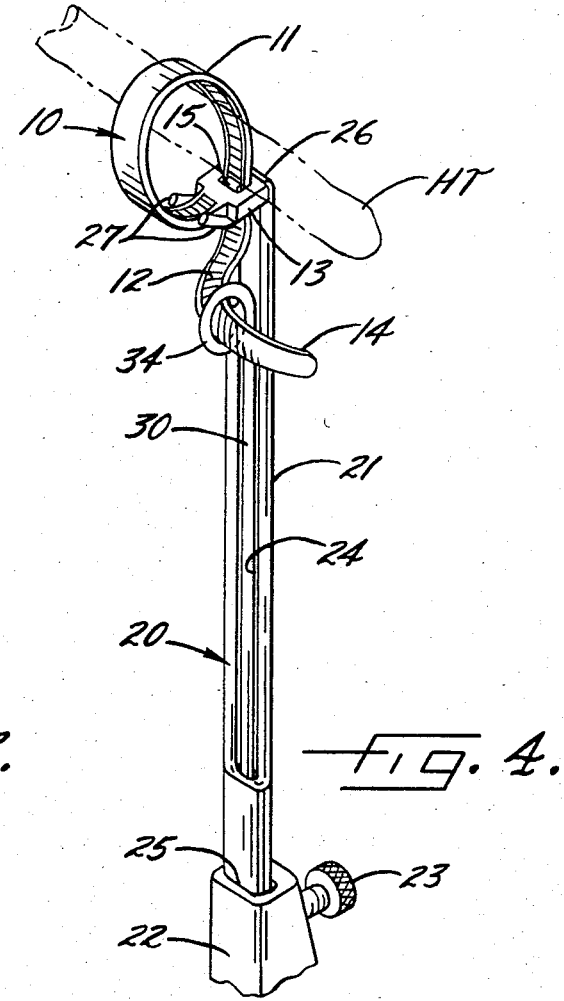
FIG. 4 is a partial plan view of the instrument illustrating the tying operation.

The instrument for performing the tying operation is shown in FIG. 3. In the embodiment shown, one end of an extension 21 is adjustably secured to a holder 22 by a set screw 23. The extension is preferably a tubular sleeve having an open channel 24 as shown in FIG. 4. The length of the extension 21 projecting beyond the holder 22 may be adjusted either by loosening the set screw 23 and moving the extension through the guideway 25, or by replacing the extension with one of a different length. The other end of the extension is bent at a right angle and bifurcated to form a fork-like construction 26 having tines 27 for holding the head of the tie while the loop is placed around the hemorrhoidal tissue and tightened. It is contemplated that the head of the tie may be wedged between the tines 27, or placed against the outward, presented face of the tines as shown in FIG. 4.

A rod 30 is movable within the tubular extension 21. One end of the rod 30 is adjustably secured to a slide 31 by means of a set screw 32, the slide being adapted to slide on the holder 22. Like the extension, the length of the rod 30 may be adjusted either by loosening the set screw 32 and moving the rod through the guideway 33, or by replacing the rod with one of a different length. The other end of the rod 30 is bent to form a buckle-like construction 34, which is slidable within the channel 24 and projects beyond the outer surface of the extension 21, for holding the free end of the looped tie during the tying operation.

According to the invention, handle means are provided to effect the movement of the rod 30 relative to the extension 21 so as to pull the strap through the head of the tie, thus tightening the loop around the hemorroidal tissue. While one skilled in the art will appreciate that any of a variety of arrangements might be employed, one type of handle means considered to be particularly advantageous is shown in FIG. 3. The handle means shown comprises ring grips 40, 41 mounted on opposite sides of the slide 31 and a ring grip 42 at the free end of the holder 22. By inserting the thumb into ring 42, and the index and middle fingers into rings 40, 41, the buckle-like construction 34 at the end of the rod 30 can be moved relative to the fork-like construction 26 at the end of the extension 21.

As best illustrated in FIG. 4, the head 13 of the looped tie is placed against the fork-like construction 26, and the strap 11 is threaded between the tines 27. The free end of the strap is threaded through the buckle-like construction 34. As shown in FIG. 4, the loop is then placed around the bulging hemorrhoidal tissue denoted generally as HT. When the rod 30 is moved away from the tines 27 by bringing ring grips 40, 41 closer to ring grip 42, the loop of the tie is tightened so as to ligate the hemorrhoidal tissue HT. After the instrument is removed from the tie, the depending end of the tie may be cut close to the head 13. The ligated tissue will become necrotic with 7 to 10 days and both the tissue and tie will slough off.

The instrument according to the invention is preferably made of stainless steel to withstand steam sterilization, although a variety of other materials might be employed. The tie is typically made of a plastic material such as a nylon, polypropylene or polyethylene. No sterilization of the tie is necessary when used in the performance of a hemorrhoidectomy. Gas sterilization of the tie is possible when ligating other live tissue.

Definitions

As used herein, the terms "ligating" and "tying" both denote a binding operation and are used interchangeably.

I claim as my invention:

1. A process for ligating live tissue using an elongated strap having first and second ends, said process comprisising the following steps:

threading said first end of said strap through an apertured head in said second end of said strap thereby engaging teeth along the length of said strap with a pawl associated with said apertured head so as to lock the strap into a looped configuration;

placing the loop around the live tissue; and pulling the first end of the strap so as to tighten the loop around the live tissure.

2. A process of ligating live tissue using an elongated toothed strap having first and second ends and an instrument including an extension for tightening a loop formed from said strap, said process comprising the following steps:

forming a loop with said toothed strap by threading the first end of the strap through an apertured head of said second end, the strap being locked in a loop configuration by a pawl in said head engaging the teeth distributed along the length of said strap;

placing the apertured head in a holding means of said extension and fixing said second end of said strap to a rod adapted for movement relative to said extension;

placing the loop around the live tissue; and moving the rod relative to the extension to pull the length of the strap through the head of said strap so as to tighten the loop about said tissue.

3. A process as claimed in claim 1 wherein the serrations of teeth of said strap are recessed into the body of said strap so as to guard against the serrations ripping the live tissue.

* * * * *